US007035414B2

(12) United States Patent
Daly

(10) Patent No.: US 7,035,414 B2
(45) Date of Patent: Apr. 25, 2006

(54) ACTIVE NOISE ATTENUATION SYSTEM

(75) Inventor: Paul D. Daly, Troy, MI (US)

(73) Assignee: Siemens VDO Automotive Inc., Chatham (CA)

(*) Notice: Subject to any disclaimer, the term of this patent is extended or adjusted under 35 U.S.C. 154(b) by 786 days.

(21) Appl. No.: 09/795,595

(22) Filed: Feb. 28, 2001

(65) Prior Publication Data

US 2002/0039423 A1 Apr. 4, 2002

Related U.S. Application Data

(60) Provisional application No. 60/193,225, filed on Mar. 30, 2000.

(51) Int. Cl.
*A61F 11/06* (2006.01)

(52) U.S. Cl. .................................... 381/71.4; 381/71.5

(58) Field of Classification Search ............... 381/71.5, 381/71.1, 71.4; 181/206
See application file for complete search history.

(56) References Cited

U.S. PATENT DOCUMENTS

| | | | | |
|---|---|---|---|---|
| 5,446,790 | A | 8/1995 | Tanaka et al. | |
| 5,513,266 | A * | 4/1996 | Zuroski | 381/71.5 |
| 5,600,106 | A * | 2/1997 | Langley | 181/206 |
| 5,713,322 | A | 2/1998 | Mausner | |
| 5,828,759 | A | 10/1998 | Everingham | |
| 5,850,458 | A * | 12/1998 | Tomisawa et al. | 381/71.4 |
| 6,084,971 | A * | 7/2000 | McLean | 381/71.5 |
| 6,605,131 | B1 * | 8/2003 | Vanderveen et al. | 381/71.5 |

FOREIGN PATENT DOCUMENTS

| | | |
|---|---|---|
| EP | 0624722 A1 | 11/1994 |
| EP | 0884471 A2 | 12/1998 |
| WO | WO 00/04532 | 1/2000 |

OTHER PUBLICATIONS

European Search Report, dated Jul. 15, 2002.

* cited by examiner

*Primary Examiner*—Brian T. Pendleton

(57) ABSTRACT

An active noise attenuation system for an air induction assembly includes a housing that is mounted to a vehicle structure and a speaker assembly that is mounted within the housing to generate a sound field for attenuating noise. The housing defines an air inlet duct open end through which air is drawn. A microphone detects noise and modifies an anti-noise signal that is sent from an electronics center. The electronics center receives the signal, mixes with other engine signals, phase-shifts the signal, and sends the phase-shifted signal to the speaker to attenuate the noise. The speaker includes electrical connections that extend outwardly toward the air inlet duct open end for connection to the electronics center. The microphone and speaker are connected to the electronics center with flex cables.

20 Claims, 2 Drawing Sheets

ACTIVE NOISE ATTENUATION SYSTEM

RELATED APPLICATION

This application claims priority to provisional application No. 60/193,225 filed on Mar. 30, 2000.

BACKGROUND OF THE INVENTION

1. Field of the Invention

This invention relates to a method and apparatus for assembling an active noise attenuation system for an air induction system. Specifically, a speaker is assembled into a housing and includes front facing electrical connectors for connection to a controller.

2. Related Art

Internal combustion engines include air induction systems for conducting air to engine cylinders. Engine noise is propagated through the air induction systems, which is undesirable. Noise attenuation mechanisms have been installed within the air induction systems to reduce these noises. Typically these noise attenuation mechanisms include a speaker, a microphone, and a signal generator that are mounted within an air inlet duct housing. The microphone detects the noise and generates a noise signal that is sent to the signal generator. The signal generator phase-shifts the signal and sends the signal to the speaker to generate a sound field that cancels out the noise that is being detected by the microphone.

The signal generator is part of an electronics center that is mounted inside the air inlet duct housing behind the speaker. Typically, the speaker includes a wire connector that extends off the back of the speaker to engage a corresponding connector on the electronics center. This connection orientation results in a time consuming and difficult assembly process. Additionally, the noise attenuation system is difficult to repair because the electronics center is mounted behind the speaker.

It is the object of the present invention to provide a simple and effective apparatus and method to assemble the speaker within the housing that overcomes the deficiencies outlined above. Further, this method will allow repairs to the system to be easily performed.

SUMMARY OF THE INVENTION

In a disclosed embodiment of this invention, an active noise attenuation system includes an air inlet duct housing having an open end into which air is drawn. A speaker is mounted within the air inlet duct and includes a first connector extending toward the open end of the housing. A sound detector senses noise that emanates from the air flow duct housing to generate a corresponding noise signal. A controller has a second connector for engaging the first connector to electrically connect the controller to the sneaker. The controller receives the signal and phase shifts the signal to attenuate the noise emanating for the air inlet duct. Preferably, the first connector includes at least one wire that extends outward from a central location within the speaker towards the open end or front of the air inlet duct housing. A flex cable is used to interconnect the first and second connectors.

In a preferred embodiment, the controller includes a controller housing that is mounted to an external surface of the air inlet duct housing. A printed circuit board and heat conducting foam are installed within the controller housing and a controller housing cover is snap-fit to the controller housing.

In one embodiment, the sound detector is mounted on a support arm that is attached to controller housing. The support arm positions the sound detector at a location between the speaker and the open end of the air inlet duct housing.

A method for assembling an active noise attenuation system includes the following steps. The air inlet duct housing is mounted to a vehicle structure and the speaker assembly is positioned within the air inlet duct housing such that a speaker face defines a plane that faces the open end of the air inlet duct housing. The sound detector is supported by the housing and generates a signal corresponding to noise from the airflow duct housing. The controller is connected to the speaker assembly through an electrical connection extending outwardly through a front plane of the speaker. The controller phase shifts the noise signal to attenuate the noise emanating from the air inlet duct housing.

The preferred method includes mounting a controller housing to an external surface of the air inlet duct housing, installing a printed circuit board and heat conducting foam within the controller housing, and snap-fitting a housing cover to the controller housing to enclose the printed circuit board within the controller housing. The sound detector is supported on an arm extending from the housing cover and is positioned between the speaker face and the open end of the air inlet duct housing.

The subject apparatus provides a simple method for assembling an active noise attenuation system. As a result, repairs and adjustments can easily be made without requiring extensive disassembly.

These and other features of the present invention can be best understood from the following specification and drawings, the following of which is a brief description.

DETAILED DESCRIPTION OF AN EXEMPLARY EMBODIMENT

Figure 1:
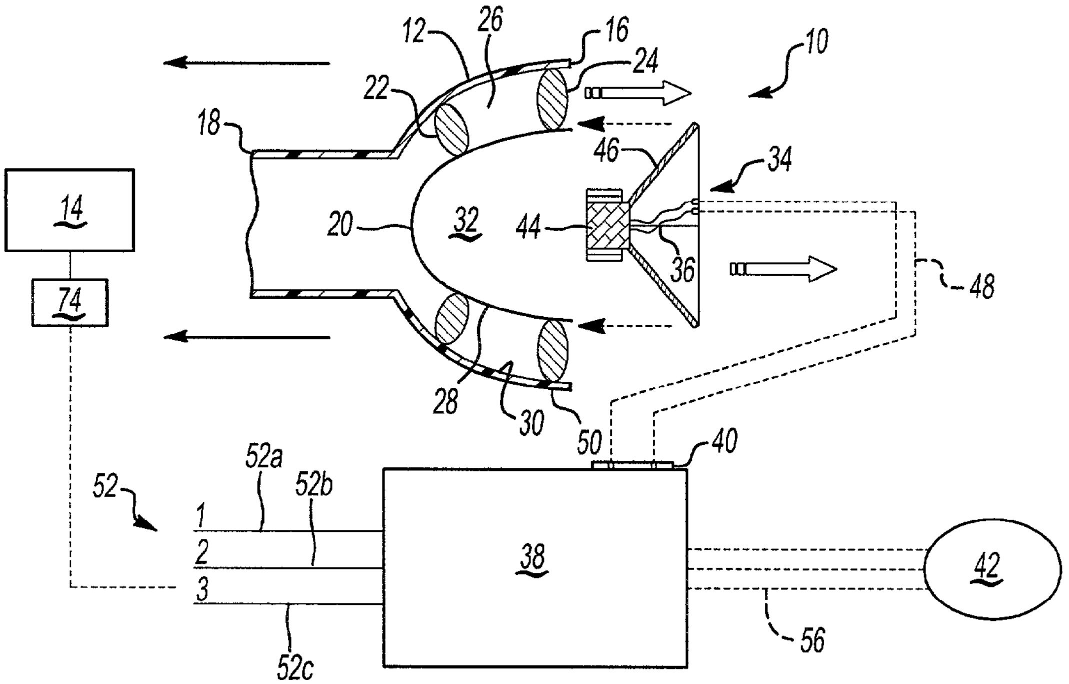
FIG. 1 is a schematic diagram of a disassembled noise attenuation system incorporating the subject invention.

Referring to the drawings, FIG. 1 shows a noise attenuation system 10 including an air inlet duct housing 12 forming part of an air induction system for an internal combustion engine 14. The air inlet duct housing 12 has an open forward facing end 16 and a rearward end 18 that faces the engine 14. The forward facing end 16 is of greater diameter than the rearward end 18.

Mounted within the air inlet duct housing 12 is a mid-body portion 20. The mid-body portion 20 is concentrically positioned within air inlet duct housing 12 on a pair of integrally formed struts 22, 24 to define an annular passage 26 between an exterior surface 28 of the mid-body portion 20 and an interior surface 30 of the air inlet duct housing 12. The mid-body portion 20 is preferably parabola shaped to define a central chamber 32 with a tapered bottom end facing the engine 14 and an open end facing away from the engine 14.

A speaker assembly 34 is mounted within the chamber 32 and includes a speaker connector 36 that extends outwardly from the speaker 34 towards the open forward facing end 16 of air inlet duct housing 12. An electronics center 38 is operably connected to the speaker 34 via a connector 40. The electronics center 38 can include a controller, microprocessor unit, or other similar device whose operation is well known in the art.

A sound detector 42, such as a microphone for example, is mounted within the air induction system to sense noise emanating from the engine 14. The sound detector 42 generates a noise signal that is sent to the electronics center 38 where the signal is phase-shifted by approximately 180 degrees. The phase-shifted signal is then sent to the speaker 34 to generate a sound field that cancels out or attenuates the noise detected by the sound detector 42.

Figure 2:
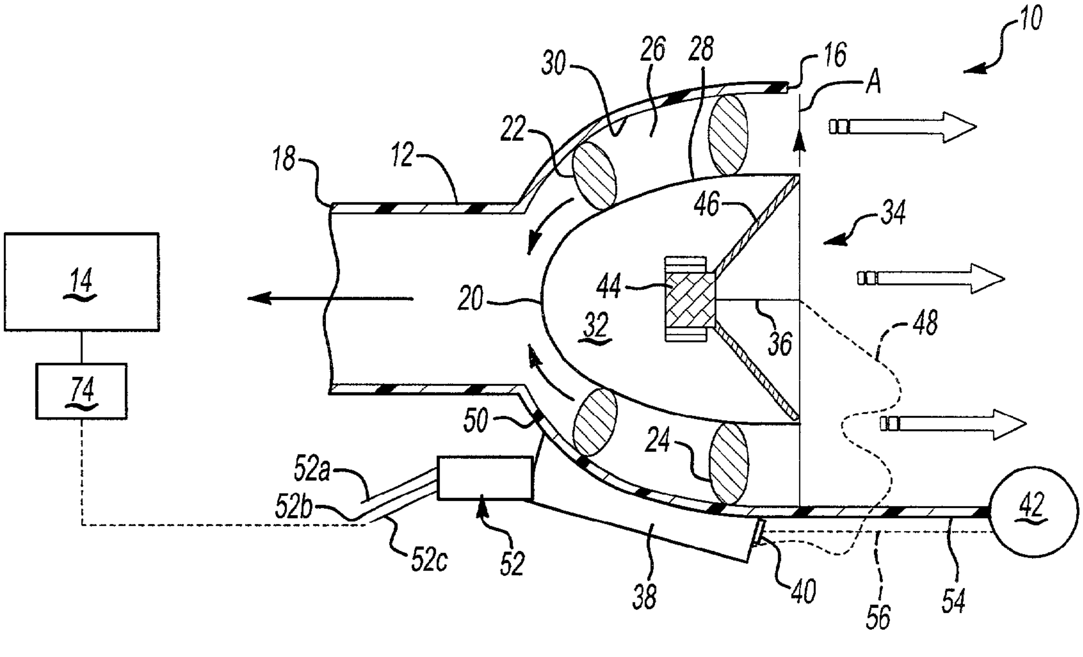
FIG. 2 is similar to FIG. 1 but shows an assembled system.

As shown in FIG. 2, the speaker 34 is assembled right to left into the air inlet duct housing 12. The speaker assembly 34 includes a base portion 44 radiating outwardly into a frustro-conical speaker portion 46 that defines a plane A near the open end 16 of the air inlet duct housing 12). The plane A is preferable co-planar with the open end face of the mid-body portion 20 once the speaker 34 is assembled into the housing 12. The speaker connector 36 extends outwardly from the base 44 adjacent to the plane A and is connected to the electronics center connector 40. The forward facing speaker connector 36 is preferably formed as a wire connection having at least one wire that is connected to the electronics center connector 40. Preferably, a flex cable or flex circuit 48 interconnects the two connectors 36, 40 to facilitate assembly. Because the speaker connector 36 has front mount wires, the speaker 34 is easily assembled right to left into the air inlet duct housing 12.

The electronics center 38 is mounted to an exterior surface 50 of the air in let duct housing 12 and includes a plurality of connections 52 for interfacing with various vehicle components. Preferably, there are at least three (3) connections 52. One connection 52*a* is to ground, one connection 52*b* is to a battery for power, and one connection 52*c* is a serial port interface for connection to an engine management control system 74.

The sound detector 42 is preferably mounted adjacent to the annular passage 26 in a forward position extending beyond plane A. The sound detector 42 can be supported on an arm 54 that mounts the air inlet duct housing 12. The arm 54 can be a separate piece or integrally formed with the housing 12 as one piece. A flex cable or flex circuit 56 preferably interconnects the sound detector 42 to the electronics center 38.

Figure 3:
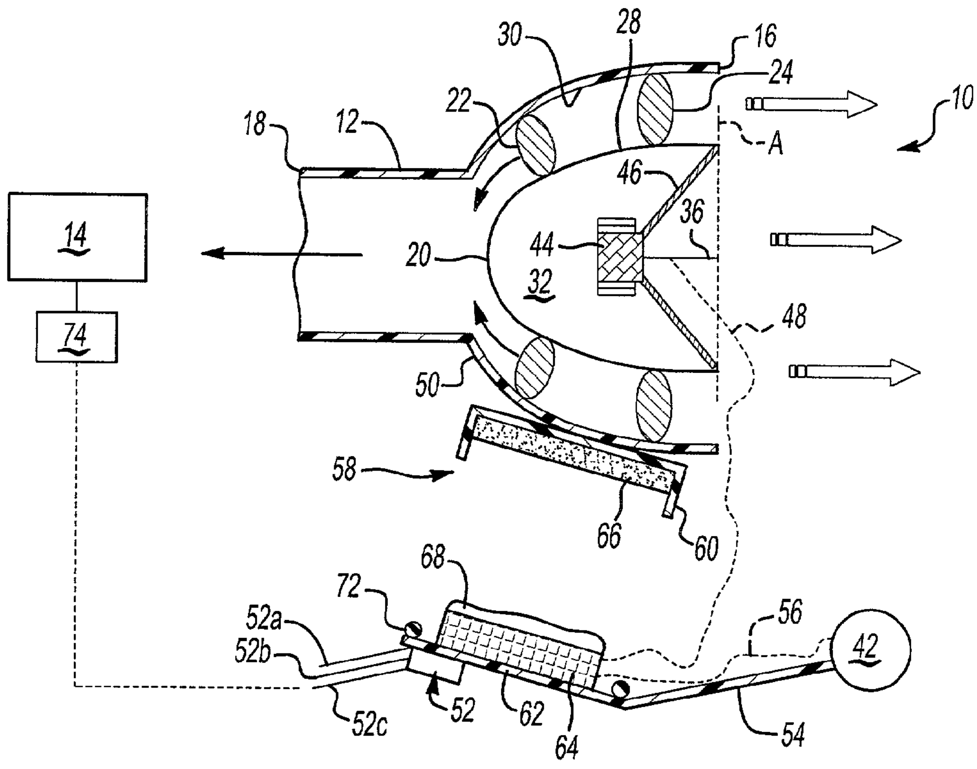
FIG. 3 is a schematic diagram of the disassembled noise attenuation system with an externally mounted controller housing.

As shown in FIG. 3, the electronics center 38 is preferably mounted within a controller housing 58 mounted to the exterior surface 50 of the air inlet duct housing 12. The controller housing 58 includes a base portion 60 and a snap-fit cover 62. The electronics center 38 including a printed circuit board 64, heat conducting foam 66, and other known electronic components 68 are installed and sealed with a seal 72 within the controller housing 58. The air inlet duct housing 12 and controller housing 58 are preferably made from plastic with the controller housing being welded to or otherwise joined to the air inlet duct housing 12 by means well known in the art.

Figure 4:
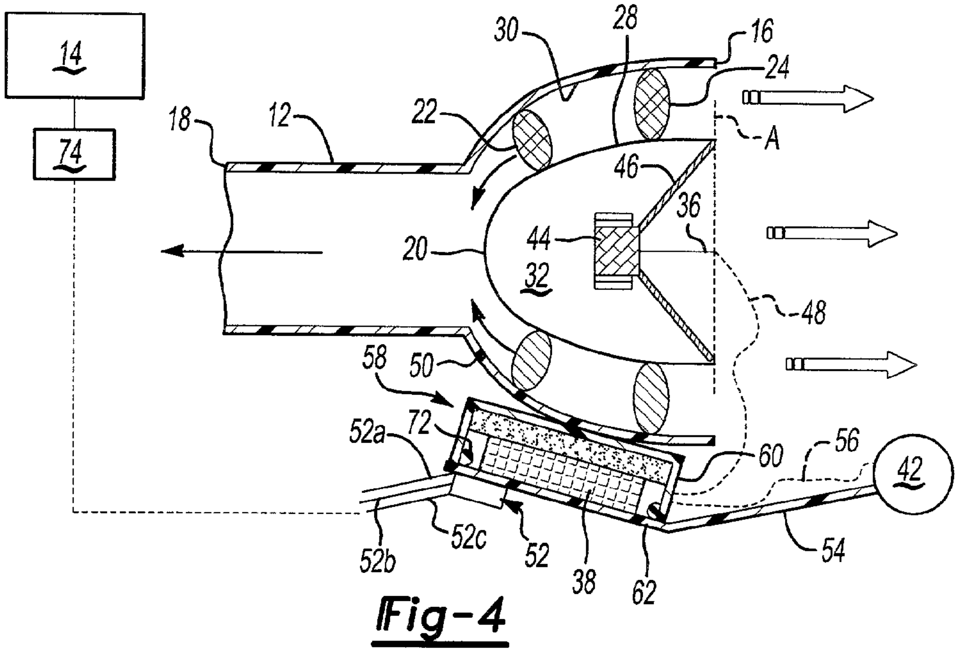
FIG. 4 is similar to FIG. 3 but shows an assembled system.

As shown in FIG. 4, the housing cover 62 is snap fit into place to enclose and seal the electronics center 38 within the controller housing 58. As discussed above the sound detector 42 can be mounted to the air inlet duct housing 12 or optionally can be mounted to the controller housing 58. The support arm 54 can be attached to the base portion 60 or the snap-fit cover 62. The connections 52 are preferably mounted to an external surface of the snap-fit cover 62 and can be integrally formed with the cover 62 as one piece to facilitate assembly The method for assembling the active noise attenuation system includes the following steps. The air inlet duct housing 12 is mounted to the vehicle structure 76. The speaker assembly 34 is positioned within the air inlet duct housing 12 such that a speaker face defining the plane A is facing the open end 16. The sound detector 42 is supported on the housing 12 to generate a noise signal corresponding to noise caused by airflow through the air inlet duct housing 12. The electronics center 38 is connected to the speaker assembly 34 through an electrical connection extending outwardly toward the plane A to phase shift the noise signal.

Additional steps include concentrically mounting the speaker 34 to the mid-body portion 20 concentrically formed within the air inlet duct housing 12 to define the annular flow passage 26 between the housing 12 and the mid-body portion 20. The sound detector 42 is positioned beyond the open end 16 and the plane A. Further steps include mounting the controller housing 58 to the exterior surface 50 of the air inlet duct housing 12, installing a printed circuit board 64 and heat conducting foam 66 within the controller housing 58, and snap-fitting the housing cover 62 to the controller housing to enclose the printed circuit board 64 within the controller housing 58. A support arm 54 for the sound detector 42 can be extended or supported from the housing cover 62 or the air inlet duct housing 12. The speaker 34 and sound detector 42 are connected to the controller with flex cables or flex circuits.

The subject invention provides a simple method for assembling a speaker into an air inlet duct housing for an active, noise attenuation system from a right to left orientation. As a result, repairs and adjustments can easily be made without requiring extensive disassembly.

Although a preferred embodiment of this invention has been disclosed, it should be understood that a worker of ordinary, skill in the art would recognize many modifications come within the scope of this invention. For that reason, the following claims should be studied to determine the true scope and content of this invention.

What is claimed is:

1. An active noise attenuation system comprising:
- an air inlet duct housing having an open end into which air is drawn;
- a speaker mounted within said air inlet duct and including a first connector extending toward said open end;
- a sound detector for sensing noise emanating from said air inlet duct and generating a noise signal corresponding to said noise; and
- a controller having a second connector for engaging said first connector to electrically connect said controller to said speaker, said controller for receiving and phase shifting said noise signal to attenuate said noise emanating for said air inlet duct.

2. A system according to claim 1 wherein said controller is mounted on an external surface of said housing.

3. A system according to claim 2 wherein said controller includes a printed circuit board partially surrounded by heat conducting foam and a controller housing that is attached to said external surface.

4. A system according to claim 3 wherein said controller housing includes a snap-fit cover and seal for enclosing said printed circuit board within said controller housing.

5. A system according to claim 4 including a plurality of interface connections integrally formed within said cover as one piece.

6. A system according to claim 1 wherein said speaker has a base portion radiating outwardly into a frustro-conical speaker portion defining a plane near said open end, said first connector including a wire assembly extending outwardly from said base portion and adjacent to said plane.

7. A system according to claim 6 including a mid-body portion concentrically mounted within said air inlet duct housing to define an annular flow passage between said housing and said mid-body portion, said speaker being concentrically mounted within said mid-body portion.

8. A system according to claim 7 wherein said sound detector includes a microphone supported by said housing and positioned beyond said plane adjacent to said open end.

9. A system according to claim 8 including a first flexible cable interconnecting said first and second connectors and a second flexible cable interconnecting said microphone to said controller.

10. A system according to claim 1 wherein said speaker includes a base portion and a speaker portion, said first connector extending outwardly from said base portion toward said speaker portion.

11. A system according to claim 10 wherein said sound detector is positioned adjacent said speaker portion at said open end with said first connector extending in a direction toward said sound detector.

12. A system according to claim 10 wherein said speaker portion includes a speaker face defining a plane with said first connector extending outwardly toward said plane.

13. A system according to claim 1 wherein said controller includes a first interface connection for communication with a battery, a second interface connection to ground, and a third interface connection for a serial for interface that communicates with an engine management system.

14. A system according to claim 1 wherein said speaker has a base portion radiating outwardly into a speaker portion that is wider than said base portion, and wherein said speaker portion directly faces said open end of said air inlet duct housing.

15. A method for assembling an active noise attenuation system comprising the steps of:

(a) mounting an air inlet duct housing having an open end into which air is drawn to a vehicle structure;

(b) positioning a speaker assembly within the air inlet duct housing such that a speaker face defining a plane is facing the open end;

(c) supporting a sound detector on the housing to generate a noise signal corresponding to noise caused by airflow through the air inlet duct housing; and (d) connecting a controller to the speaker assembly trough an electrical connection extending outwardly from the speaker assembly toward the plane to phase shift the noise signal.

16. A method according to claim 15 wherein step (d) includes mounting a controller housing to an external surface of the air inlet duct housing, installing a printed circuit board and heat conducting foam within the controller housing, and snap-fitting a housing cover to the controller housing to enclose the printed circuit board within the controller housing.

17. A method according to claim 16 including the step of extending a support arm for the sound detector from the housing cover.

18. A method according to claim 15 wherein step (b) includes concentrically mounting the speaker assembly to a mid-body portion concentrically formed within the air inlet duct housing to define an annular flow passage between the housing and the mid-body portion.

19. A method according to claim 15 wherein step (c) includes positioning the sound detector forwardly beyond the open end and the plane.

20. A method according to claim 15 including connecting the speaker assembly to the controller with a first flex cable and connecting the sound detector to the controller with a second flex cable.

* * * * *